US012567268B2

(12) United States Patent
Ma et al.

(10) Patent No.: US 12,567,268 B2
(45) Date of Patent: Mar. 3, 2026

(54) AUTOMATED NANOSCOPY SYSTEM HAVING INTEGRATED ARTIFACT MINIMIZATION MODULES, INCLUDING EMBEDDED NANOMETER POSITION TRACKING BASED ON PHASOR ANALYSIS

(71) Applicant: UNIVERSITY OF PITTSBURGH—OF THE COMMONWEALTH SYSTEM OF HIGHER EDUCATION, Pittsburgh, PA (US)

(72) Inventors: Hongqiang Ma, Pittsburgh, PA (US); Yang Liu, Sewickley, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 327 days.

(21) Appl. No.: 18/553,578

(22) PCT Filed: May 16, 2022

(86) PCT No.: PCT/US2022/029369
§ 371 (c)(1),
(2) Date: Oct. 2, 2023

(87) PCT Pub. No.: WO2022/245689
PCT Pub. Date: Nov. 24, 2022

(65) Prior Publication Data
US 2024/0185625 A1     Jun. 6, 2024

Related U.S. Application Data

(60) Provisional application No. 63/190,452, filed on May 19, 2021.

(51) Int. Cl.
*G06V 20/69*      (2022.01)
*G02B 21/36*      (2006.01)
(Continued)

(52) U.S. Cl.
CPC ......... *G06V 20/693* (2022.01); *G02B 21/362* (2013.01); *G06T 5/10* (2013.01);
(Continued)

(58) Field of Classification Search
CPC ...... G06V 20/693; G06V 10/25; G06V 20/70; G06V 10/60; G06V 20/69; G06V 20/60;
(Continued)

(56) References Cited

U.S. PATENT DOCUMENTS 8,184,367 B2 * 5/2012 Rolland ............... A61B 5/0075
                                                                                 359/383
10,325,753 B2 * 6/2019 Masnaghetti ........... H01J 37/28
(Continued)

FOREIGN PATENT DOCUMENTS

KR      20240023042 A  *  2/2024  ............. G02B 21/83
WO      WO-2010105015 A2 *  9/2010  ............. G06T 7/246
WO      2021034569 A2     2/2021

OTHER PUBLICATIONS

Bernd; Rieger et al. "Image Processing and Analysis for Single-Molecule Localization Microscopy: Computation for nanoscale imaging", Dec. 2014, IEEE (Year: 2014).*
(Continued)

*Primary Examiner* — Aaron W Carter
*Assistant Examiner* — Alejandro Hernandez
(74) *Attorney, Agent, or Firm* — Philip E. Levy; Eckert Seamans Cherin & Mellott, LLC

(57) ABSTRACT

A method of compensating for focus drift in a microscopy system includes receiving data representing a reference light signal reflected from a sample and received by an image sensor, identifying from the data a peak of the reference light signal, the peak having a maximum intensity value for the reference light signal, extracting a sub-region having a center from the data, the center being located at the peak, (Continued)

calculating a first harmonic of a Fourier transform of the extracted sub-region, estimating a peak position of the reference light signal based on a phase of the first harmonic, and moving the lens system of the microscopy system or the sample in the axial direction using the translation stage based on the estimated position. Also, a system compensating for focus drift in a microscopy system according to the above method.

25 Claims, 4 Drawing Sheets

(51) Int. Cl.

| | | |
|---|---|---|
| *G06T 5/10* | (2006.01) | |
| *G06V 10/25* | (2022.01) | |
| *G06V 10/60* | (2022.01) | |
| *G06V 20/70* | (2022.01) | |
| *G16H 30/40* | (2018.01) | |

(52) U.S. Cl.
CPC .............. *G06V 10/25* (2022.01); *G06V 10/60* (2022.01); *G06V 20/70* (2022.01); *G16H 30/40* (2018.01)

(58) Field of Classification Search
CPC .. G16H 30/40; G02B 21/362; G02B 21/0052; G02B 21/0032; G06T 5/10; G01N 21/6458; G01N 21/62
See application file for complete search history.

(56) References Cited

U.S. PATENT DOCUMENTS

| | | | | |
|---|---|---|---|---|
| 2005/0141080 A1* | 6/2005 | Kohno | ............... | G02B 21/0032 359/368 |
| 2006/0192947 A1 | 8/2006 | Roberts et al. | | |
| 2007/0165221 A1* | 7/2007 | Deck | .................... | G01J 3/0289 356/326 |
| 2008/0116392 A1* | 5/2008 | Brooker | ............. | G02B 21/0076 359/356 |
| 2013/0321907 A1* | 12/2013 | Kennedy | .............. | G02B 21/082 359/379 |
| 2017/0084424 A1* | 3/2017 | Masnaghetti | ........... | H01J 37/28 |
| 2018/0164569 A1* | 6/2018 | Brinkman | .............. | G02B 21/16 |
| 2018/0314045 A1 | 11/2018 | Bernal Arango | | |
| 2021/0056287 A1* | 2/2021 | Schaumburg | ........ | G06V 20/695 |
| 2022/0138945 A1* | 5/2022 | Luengo Hendriks | .. | G06V 20/70 382/133 |
| 2024/0248291 A1* | 7/2024 | Harke | ................ | G02B 27/0933 |
| 2024/0393249 A1* | 11/2024 | Schonle | ............. | G02B 21/0076 |
| 2025/0150716 A1* | 5/2025 | Viering | ................ | H04N 23/555 |

OTHER PUBLICATIONS

H. Deschout, F. C. Zanacchi, M. Mlodzianoski, A. Diaspro, J. Bewersdorf, S. T. Hess, and K. Braeckmans, Nat. Methods 11, 253 (2014).

S. Coelho, J. Baek, M. S. Graus, J. M. Halstead, P. R. Nicovich, K. Feher, H. Gandhi, J. J. Gooding, and K. Gaus, Sci. Adv. 6, eaay8271 (2020).

H. Ma and Y. Liu, APL Photonics 5, 060902 (2020).

F. Blateyron, in Optical Measurement of Surface Topography (Springer Berlin Heidelberg, 2011), pp. 71-106.

"The Nikon Perfect Focus System (PFS) | Nikon's MicroscopyU," https://www.microscopyu.com/tutorials/the-nikon-perfect-focus-system-pfs.

"PgFocus—Wiki," http://big.umassmed.edu/wiki/index.php/PgFocus#Firmware.

R. Parthasarathy, Nat. Methods 9, 724 (2012).

H. Ma, F. Long, S. Zeng, and Z.-L. Huang, Opt. Lett. 37, 2481 (2012).

K. J. A. Martens, A. N. Bader, S. Baas, B. Rieger, and J. Hohlbein, J. Chem. Phys. 148, 123311 (2018).

B. Yu, D. Chen, J. Qu, and H. Niu, Opt. Lett. 36, 4317 (2011).

J. Bai, X. Li, X. Wang, Q. Zhou, and K. Ni, Sensors 19, 3592 (2019).

C. Chen, R. Leach, J. Wang, X. Liu, X. Jiang, and W. Lu, Opt. Lett. 46, 1616 (2021).

R. Henriques, M. Lelek, E. F. Fornasiero, F. Valtorta, C. Zimmer, and M. M. Mhlanga, Nat. Methods 7, 339 (2010).

F. Fereidouni, A. N. Bader, and H. C. Gerritsen, Opt. Express 20, 12729 (2012).

H. Ma, J. Xu, J. Jin, Y. Gao, L. Lan, and Y. Liu, Sci. Rep. 5, 14335 (2015).

H. Ma, J. Xu, and Y. Liu, Sci. Adv. 5, eaaw0683 (2019).

H. Ma, J. Xu, J. Jin, Y. Huang, and Y. Liu, Biophys. J. 112, 2196 (2017).

* cited by examiner

AUTOMATED NANOSCOPY SYSTEM HAVING INTEGRATED ARTIFACT MINIMIZATION MODULES, INCLUDING EMBEDDED NANOMETER POSITION TRACKING BASED ON PHASOR ANALYSIS

CROSS-REFERENCE TO RELATED APPLICATION

This patent application is a U.S. National Phase of International Application No. PCT/US2022/029369, filed on May 16, 2022, which claims the priority benefit under 35 U.S.C. § 119(e) of U.S. Provisional Application No. 63/190,452, filed on May 19, 2021, the contents of which are incorporated herein by reference.

GOVERNMENT CONTRACT

This invention was made with government support under grant #s CA225494, CA232593, and CA254112 awarded by the National Institutes of Health (NIH). The government has certain rights in the invention.

FIELD OF THE INVENTION

The disclosed concept relates to microscopy systems, and, in particular, to an automated nanoscopy system that, in one embodiment, integrates multiple artifact minimization modules and that provides high quality images with spatial resolution one order of magnitude better than conventional light microscopy with minimal user expertise being required. The disclosed concept also relates to a phasor-based algorithm for nanometer position tracking in microscopy systems.

BACKGROUND OF THE INVENTION

Conventional light microscopy has a limited spatial resolution of 200~500 nm, which cannot detect molecular structures. Super-resolution microscopy, also known as nanoscopy, provides much greater spatial resolution capability (e.g., down to 10 nm—an order of magnitude better than conventional light microscopy), and, as a result, has revolutionized the field of microscopy by, among other capabilities, enabling the detection of molecular structures. Current commercial super-resolution microscopy systems are, however, expensive ($300K-$500K), placing them beyond the reach of most small research laboratories. Current commercial super-resolution microscopy systems also require a dedicated room with an optical table to maintain a highly stable environment, are difficult to use, and require substantial expertise to obtain high-quality images.

Moreover, a one-dimensional (1D) position tracking system is an essential component for drift stabilization in most high-resolution microscopy systems to maintain long-term system stability. A 1D position tracking system is also commonly used in chromatic confocal microscopy for measuring nanoscale surface topography. In most drift stabilization systems, the 1D position tracking system is used to track the position of the reflected reference beam for sensing the drift of the focal plane, and the focus drift is then compensated in real time with a piezo translation stage mounted with the sample or the objective. In chromatic confocal microscopy, the spectral profile of the detected light is projected along a linear image sensor, which encodes axial positions of the sample, and the 1D position tracking system is used to detect the spectral peak of the reflected light, which is determined by the sample surface.

Existing 1D position tracking systems generally detect the reflection laser beam at the interface with a strong refractive index mismatch (either coverslip-sample or air-sample interface), which is projected onto a low-noise linear CCD sensor. A computer with a high-performance processor is often required to estimate the lateral position of the peak from the reflected signals with model-fitting based algorithms to track the axial position of the focus (or surface profile). Although such an approach can achieve the best accuracy with the theoretical minimum uncertainty, it is bulky and expensive.

SUMMARY OF THE INVENTION

These needs, and others, are met by a method of compensating for focus drift in a microscopy system, wherein the microscopy system includes a lens system and a translation stage that is structured to selectively move the lens system or a sample in an axial direction. The method includes receiving data representing a reference light signal reflected from a sample and received by an image sensor, identifying from the data a peak of the reference light signal, the peak having a maximum intensity value for the reference light signal, extracting a sub-region having a center from the data, the center being located at the peak, calculating a first harmonic of a Fourier transform of the extracted sub-region, estimating a peak position of the reference light signal based on a phase of the first harmonic, and moving the lens system or the sample in the axial direction using the translation stage based on the estimated position.

In another embodiment, a microscopy system is provided that includes a lens system, a translation stage structured to selectively move the lens system or a sample in an axial direction, an image sensor, and a control system. The control system is structured and configured for compensating for focus drift in the microscopy system by receiving data representing a reference light signal reflected from a sample and received by the image sensor, identifying from the data a peak of the reference light signal, the peak having a maximum intensity value for the reference light signal, extracting a sub-region having a center from the data, the center being located at the peak, calculating a first harmonic of a Fourier transform of the extracted sub-region, estimating a peak position of the reference light signal based on a phase of the first harmonic, and moving the lens system or the sample in the axial direction using the translation stage based on the estimated position.

In still another embodiment, a microscopy system is provided that includes an automated sample labeling module structured and configured to label fluorescence dyes to biological structures of a sample, a drift stabilization module structured and configured to actively track and compensate for focus drift of the microscopy system, an illumination module structured and configured to generate a uniform illumination field for the microscopy system, a detection module structured and configured to collect and record a fluorescence signal from the sample, an automated sample positioning module structured and configured to control a 3D position of the sample, and a control system. The control system in this embodiment includes: (i) an automated sample labelling component comprising a number of first routines for controlling the automated sample labeling module; (ii) a drift stabilization component comprising a number of second routines for controlling the drift stabilization module; (iii) an illumination control component comprising a number of third routines for controlling the illumination module; (iv) a detection component comprising a number of fourth routines for controlling the detection module; and (v) a sample positioning component comprising a number of fifth routines for controlling the automated sample positioning module.

BRIEF DESCRIPTION OF THE DRAWINGS

A full understanding of the invention can be gained from the following description of the preferred embodiments when read in conjunction with the accompanying drawings in which.

DETAILED DESCRIPTION OF THE INVENTION

Figure 1:
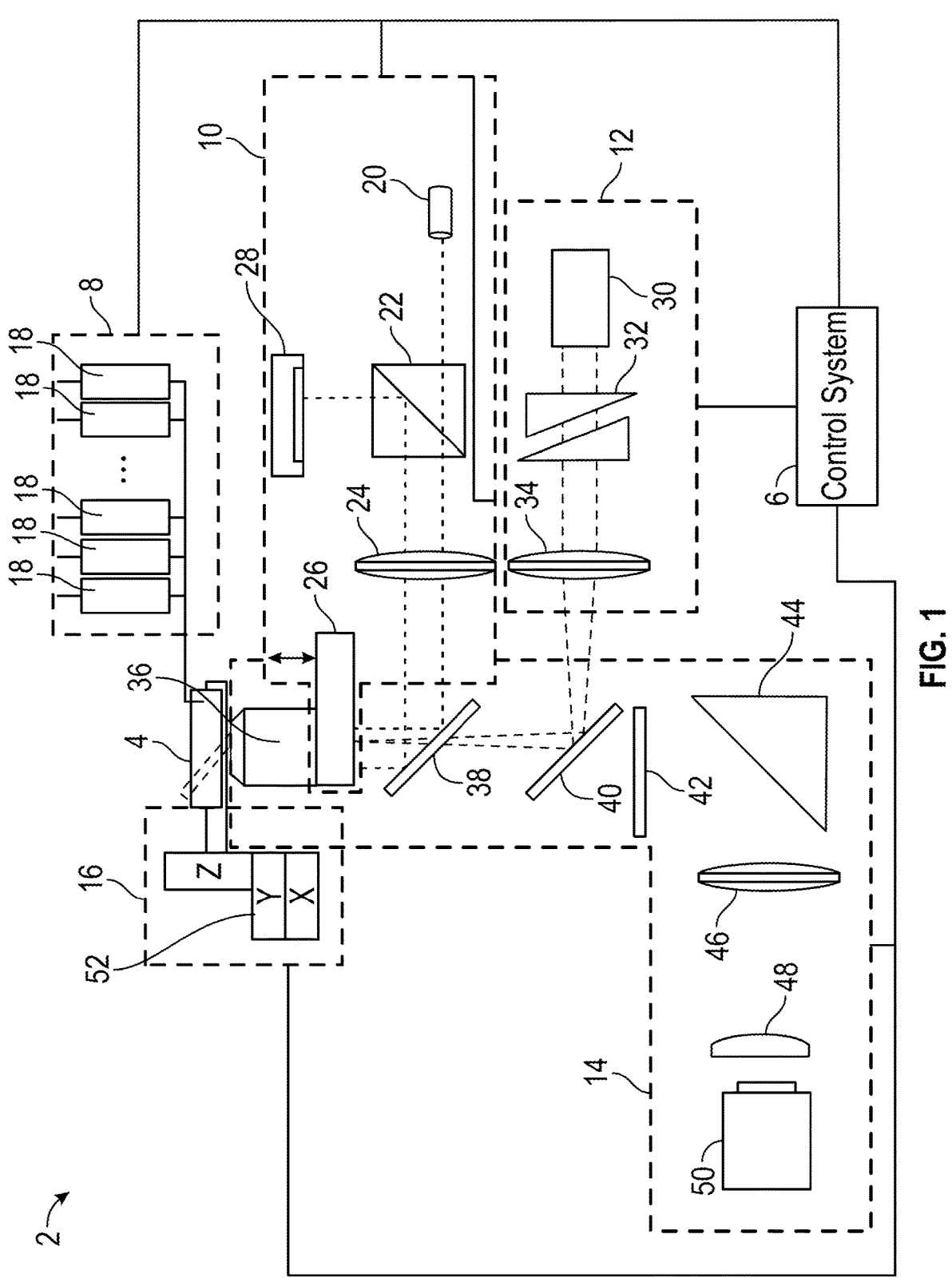
FIG. 1 is a schematic diagram of a nanoscopy system according to a non-limiting exemplary embodiment of the disclosed concept.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, the term "number" shall mean one or an integer greater than one (i.e., a plurality).

As used herein, the terms "component" and "system" are intended to refer to a computer related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers. While certain ways of displaying information to users are shown and described with respect to certain figures or graphs as screenshots, those skilled in the relevant art will recognize that various other alternatives can be employed.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept will now be described, for purposes of explanation, in connection with numerous specific details in order to provide a thorough understanding of the subject innovation. It will be evident, however, that the disclosed concept can be practiced without these specific details without departing from the spirit and scope of this innovation.

As described in greater detail herein and in Appendix A, the disclosed concept provides a low-cost, state-of-the-art nanoscopy system capable of providing a spatial resolution down to 10 nm, which is one order-of-magnitude better than conventional light microscopy systems. The cost to produce a system according to the disclosed concept is expected to be on the order of $10,000 or less, with an expected selling price on the order of $50,000 or less, which is 10 times lower than the cost of current commercial nanoscopy systems. In addition, in the exemplary embodiment, the nanoscopy system of the disclosed concept is compact and can be positioned on a regular table top without the need for a dedicated room and/or optical table. As described herein, the nanoscopy system of the disclosed concept is highly robust and automated, as it integrates a number of artifact minimization modules that provide high-quality imaging capability with minimal user expertise being required. In addition, the disclosed concept also provides a fast and precise 1D position estimation algorithm that can be implemented in an embedded position tracking system with high computational efficiency. As described in greater detail herein, the 1D position estimation algorithm estimates the position by calculating the phase shift of the first harmonic of signals in the Fourier domain.

FIG. 1 is a schematic diagram of a nanoscopy system 2 according to a non-limiting exemplary embodiment of the disclosed concept. Nanoscopy system 2 is structured and configured to obtain super resolution images from a sample that, in the exemplary embodiment, is provided within a structure such as a dish 4 (e.g., covered by a coverslip). Nanoscopy system 2 includes a control system 6, and a plurality of modules controlled by control system 6. In the exemplary embodiment, control system 6 and each of the modules controlled thereby is provided within a single housing which can be placed on a regular table top without the need for a dedicated room or optical table. As seen in FIG. 1, the modules that are provided as part of nanoscopy system 2 in the illustrated exemplary embodiment include an automated sample labeling module 8, a drift stabilization module 10, an illumination module 12, a detection module 14, and an automated sample positioning module 16. Each of these modules is described in greater detail below.

Automated sample labeling module 8 is structured and configured to automatically label fluorescence dyes to the biological structures comprising the sample that is held within dish 4. Automated sample labeling module 8 includes a plurality of micro-pumps 18 that are used to sequentially inject and/or remove various fluorescence staining reagents, imaging buffers, and/or washing buffers. In the non-limiting exemplary embodiment, each micro-pump 18 is a piezo-electrically operated pump, although other types of micro-pumps may also be employed. Micro-pumps 18 are controlled by control system 6, which accepts user commands for specific control thereof. Automated sample labeling module 8 is particularly useful for sequential multiplex imaging.

Drift stabilization module 10 is structured and configured to actively track the focus drift of nanoscopy system 2 and compensate for that drift in real time to maintain a stable imaging focus for nanoscopy system 2. As seen in FIG. 1, drift stabilization module 10 includes a light source 20, a beam splitter 22, a lens 24, a translation stage 26 (which may be, for example, and without limitation, a piezo-electrically controlled translation stage) moveable in the direction of the arrows shown in FIG. 1, which corresponds to the focus drift direction, and an embedded drift tracking system including a linear image sensor 28. In operation, reference light from light source 20 is directed to dish 4 (and the sample contained therein) by way of beam splitter 22, lens 24, and an objective lens system 36 described elsewhere herein that forms a part of detection module 14. The reference light is reflected at the surface of the coverslip of dish 4, and the movement in the axial direction of the focus (i.e., the focus drift) is then translated into the lateral movement of the reflected reference light received on linear image sensor 28. In the exemplary embodiment, the disclosed concept implements a phasor-based algorithm, described in greater detail herein, executed by control system 6 to track the focus drift in real time and to then control compensation for the detected focus drift using translation stage 26. In the exemplary embodiment, the phasor-based algorithm is able to track position with sub-pixel precision (e.g., 0.01 pixel or 1 nm, where 1 pixel equals 100 nm). As a result, drift stabilization module 10 can achieve a precision of <10 nm.

Illumination module 12 is structured and configured to generate a uniform illumination field for nanoscopy system 2 to enable super-resolution imaging. Illumination module 12 includes a laser source 30 (which may be, for example, and without limitation, a diode laser module), a prism system 32 (comprising a pair of prisms) and a lens 34. Laser source 30 outputs a Gaussian beam, which is not uniform. Illumination module 12 uses prism system 32 to reshape the laser beam from laser source 30 into a beam having a relatively uniform, rectangular shape. The intensity of laser source 30 is controlled by control system 6, and the angle of the laser beam output by laser source 30 is controlled by a stepper motor (not shown).

Detection module 14 includes an objective lens system 36, dichroic mirrors 38 and 40, an emission filter 42, a mirror 44, a tube lens 46, a cylindrical lens 48, and a camera 50 (e.g., a digital camera including a CCD in the exemplary embodiment). Detection module 14 is structured and configured to collect the fluorescence signal from the sample by way of objective lens system 36, and record the fluorescence signal using camera 50. Cylindrical lens 48 is positioned in front of camera 50 to enable 3D super-resolution imaging. In the exemplary embodiment, detection module 14 implements a robust background noise correction algorithm to enhance the quality of the images acquired with lower-cost cameras, and a fast and precise 3D localization algorithm to enable state of the art super resolution image reconstruction in real time. The background noise correction algorithm and the localization algorithm were developed by the present inventors and are described in detail in United States Patent Application Publication No. 2021/0116380, titled "Systems and Methods for Robust Background Correction and/or Emitter Localization for Super-Resolution Localization Microscopy," the disclosure of which is incorporated herein by reference.

Automated sample positioning module 16 includes a 3D translation stage 52 for controlling the 3D position of the sample under the control of control system 6. The individual translation stages of 3D translation stage 52 are mounted with stepper motors that are controlled by control system 6.

Figure 2:
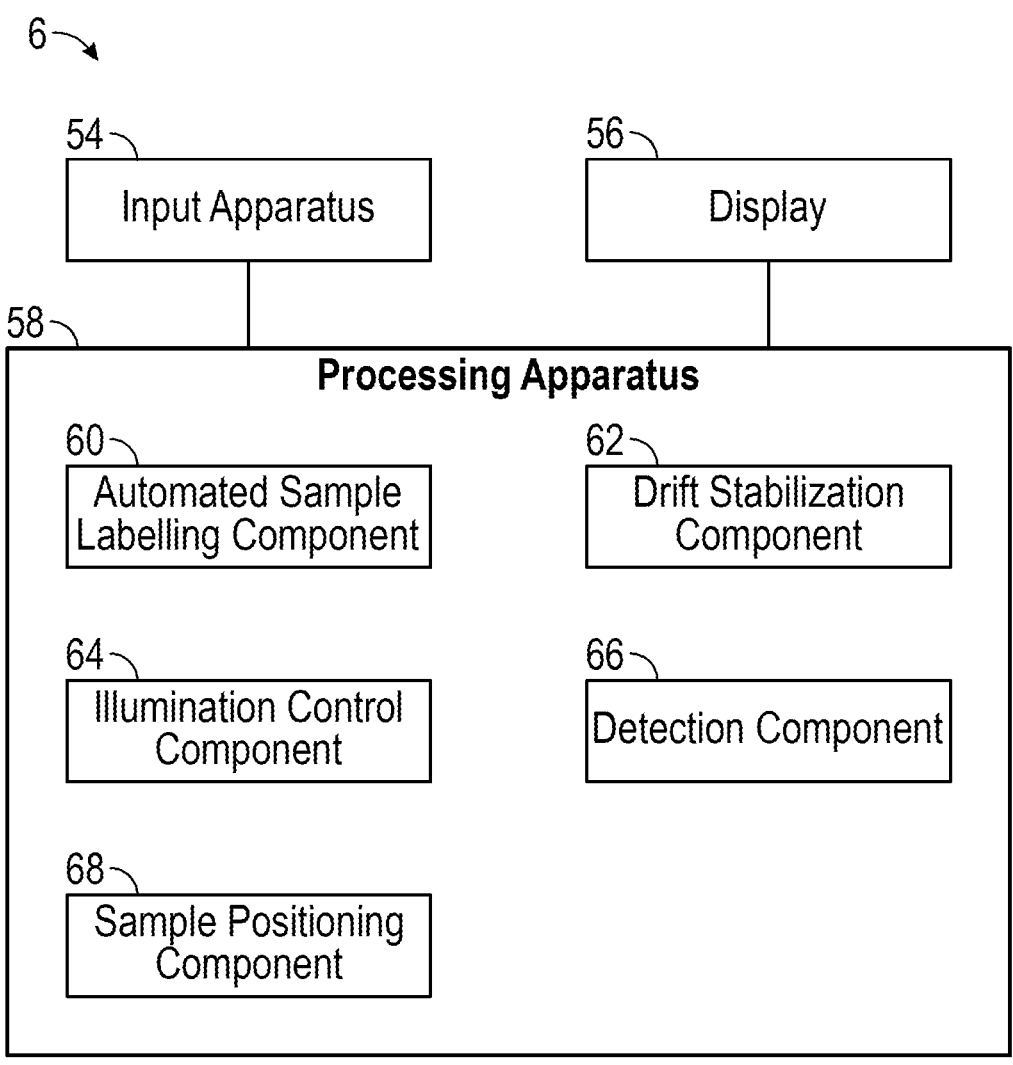
FIG. 2 is a schematic diagram of a control system for the nanoscopy system of FIG. 1 according to an exemplary embodiment of the disclosed concept.

FIG. 2 is a schematic diagram of a control system 6 according to an exemplary embodiment of the disclosed concept. As seen in FIG. 2, control system 6 is a computing device structured and configured to control the entirety of nanoscopy system 2. Specifically, control system 6 generates and sends control commands defined by the user to the various modules of nanoscopy system 2, and checks the operational status of each module of nanoscopy system 2. Control system 6 also receives data from the various modules of nanoscopy system 2 and processes such data as described herein in order to generate super resolution images. Control system 6 may be, for example and without limitation, a PC, a laptop computer, or any other suitable processing device structured and configured to perform the functionality described herein.

Referring to FIG. 2, control system 6 includes an input apparatus 54 (such as a keyboard), a display 56 (such as an LCD), and a processing apparatus 58. A user is able to provide input into processing apparatus 58 using input apparatus 54, and processing apparatus 58 provides output signals to display 56 to enable display 56 to display information to the user (such as images generated from the sample) as described herein. Processing apparatus 58 comprises a processor and a memory. The processor may be, for example and without limitation, a microprocessor (µP), a microcontroller, or some other suitable processing device, that interfaces with the memory. The memory can be any one or more of a variety of types of internal and/or external storage media such as, without limitation, RAM, ROM, EPROM(s), EEPROM(s), FLASH, and the like that provide a storage register, i.e., a non-transitory machine readable medium, for data storage such as in the fashion of an internal storage area of a computer and can be volatile memory or nonvolatile memory. The memory has stored therein a number of routines (comprising computer executable instructions) that are executable by the processor, including routines for implementing the various aspects of the disclosed concept as described herein. In particular, processing apparatus 58 includes: (i) an automated sample labelling component 60 comprising a number of routines for controlling automated sample labeling module 8 to thereby label fluorescence dyes to the biological structures comprising the sample, (ii) a drift stabilization component 62 comprising a number of routines for controlling drift stabilization module 10 to actively track and compensate for the focus drift of nanoscopy system 2, (iii) an illumination control component 64 comprising a number of routines for controlling illumination module 12 to thereby generate a uniform illumination field for nanoscopy system 2, (iv) a detection component 66 comprising a number of routines for controlling detection module 14 to collect and record the fluorescence signal from the sample, and (v) a sample positioning component 68 comprising a number of routines for controlling automated sample positioning module 16 to thereby control the 3D position of the sample. In the exemplary embodiment, drift stabilization component 62 implements the phasor-based drift tracking and compensation algorithm, also referred to herein as a phasor-based 1D position estimation algorithm, that is described in greater detail below.

Figure 3:
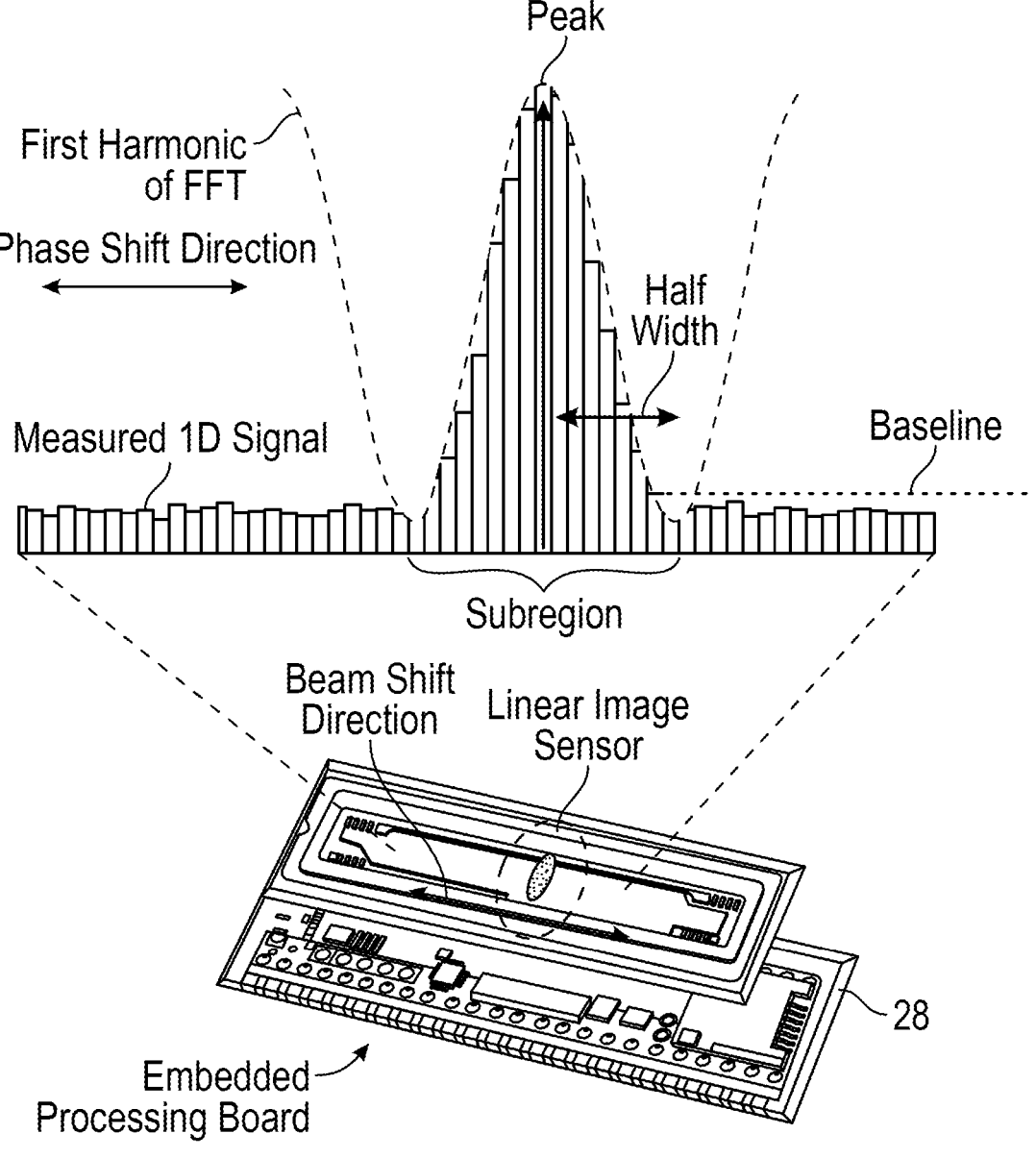
FIG. 3 is schematic diagram illustrating a phasor-based 1D position estimation algorithm according to an aspect of the disclosed concept.

The principle of the phasor-based 1D position estimation algorithm of the disclosed concept is shown in FIG. 3. The processing procedure of the phasor-based 1D position estimation algorithm comprises the following three major steps: (1) peak finding with pixel precision; (2) sub-region extraction; and (3) sub-pixel position estimation.

More specifically, in the algorithm, the raw data representing the reflected reference light is first obtained from linear image sensor 28. Then, the raw data representing the reflected reference light is searched for its maximum and minimum intensity values. The pixel with the maximum value is recognized as the peak pixel and the baseline (b) is calculated with Equation (1) below:

$$b = \min_{j=1:N}(I_j) + 0.1 \times \left(\max_{j=1:N}(I_j) - \min_{j=1:N}(I_j)\right) \tag{1}$$

where $I_j$ is the intensity of the jth pixel along the linear image sensor with N pixels. When processing weak signals, a low-pass filter (e.g., rolling average filter) can be used to suppress the high-frequency noise.

As will be appreciated, the position of the pixel with maximum value as just determined has a unit of 1 pixel (e.g., 100 nm). The disclosed concept, however, enables the retrieval of the sub-pixel position of the peak by performing the additional steps described below.

Figure 4:
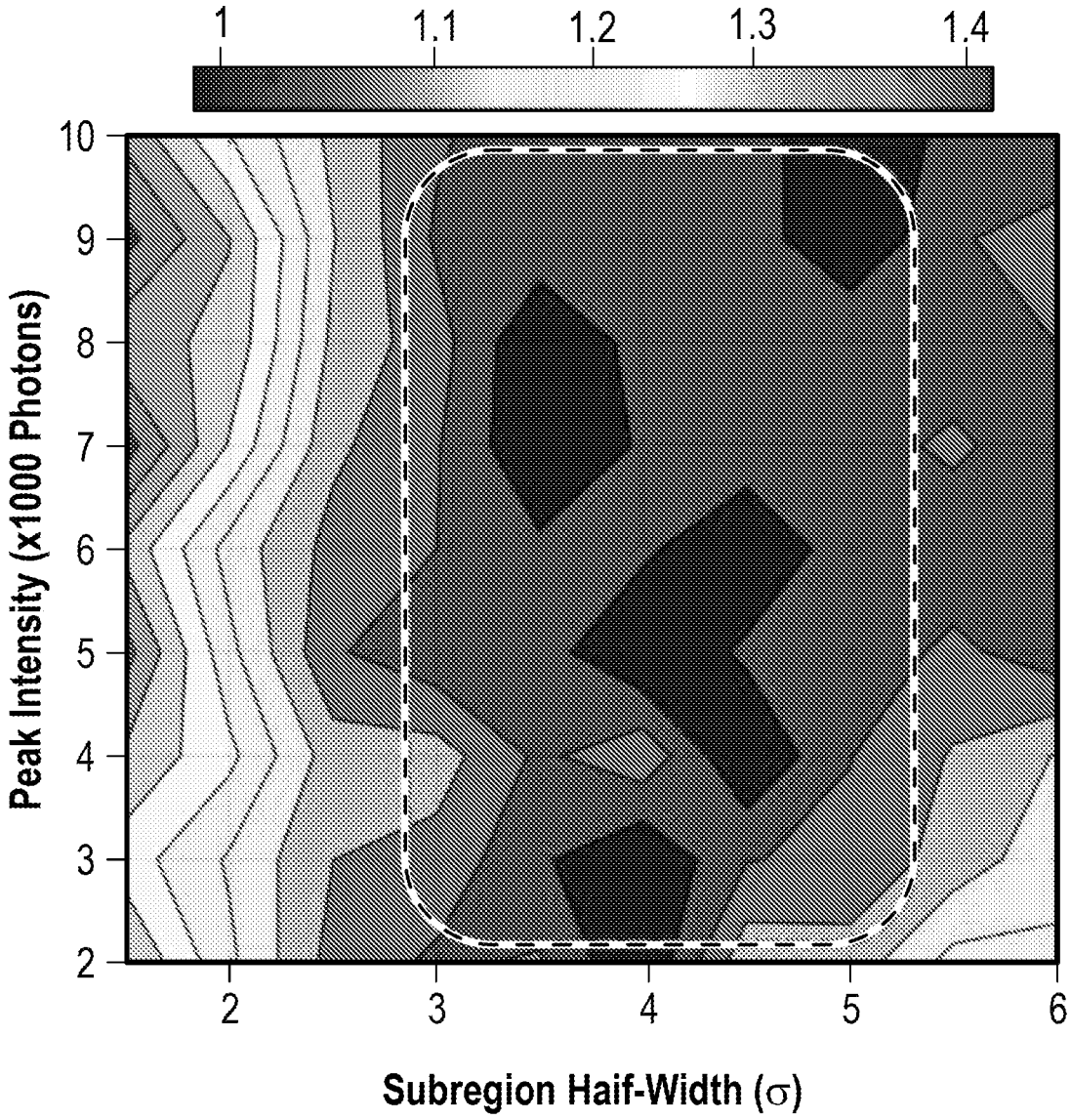
FIG. 4 is a plot illustrating that when the signal profile in the disclosed concept is approximated as a Gaussian function, the minimum errors are achieved at a region at a half width of about 3~5 times the Gaussian kernel width ($\sigma$).

Next, a sub-region is extracted from the raw data with a center at the above-recognized pixel with maximum intensity. The width of the sub-region can significantly affect the overall precision. A smaller sub-region width can miss the useful signal, while a larger sub-region width induces noisy background information, and both cases can increase estimation error. Therefore, a proper region width is important to achieve the minimum error. When the signal profile is approximated as a Gaussian function, as shown in FIG. 4, the minimum errors are achieved at a region at a half width of about 3~5 times the Gaussian kernel width ($\sigma$), which can be estimated by the Equation (2) below:

$$\begin{cases} c = \sum_{I_j>b}(I_j - b)j / \sum_{I_j>b}(I_j - b) \\ \sigma = \sum_{I_j>b}(I_j - b)|j - c| / \sum_{I_j>b}(I_j - b) \end{cases} \tag{2}$$

where b is the baseline discussed above, c is the centroid center of the signal, and $\sigma$ is the width of the Gaussian kernel. In the exemplary embodiment, a sub-region with a half width of $4\sigma$ is used to achieve the near-optimal precision for signals under various scenarios.

Finally, the first harmonic ($H_1$) of the Fourier transform of the above extracted sub-region with a width of W pixels is calculated as described in Equation (3) below:

$$H_1 = \sum_{j=1}^{W} I_j\left(\cos\left(2\pi j/W\right) - i \cdot \sin\left(2\pi j/W\right)\right) \tag{3}$$

Calculating the first harmonic of the signal as just described results in the sinusoid curve following the shape of the detected signal in the extracted region. In addition, the phase (i.e., the angle of the first harmonic) of the sinusoid curve will follow the position of the signal to follow the signal's shape, so it can be used to estimate the precise (sub-pixel) position of the signal. In particular, the phase of the first harmonic (i.e., the angle of $H_1$) can directly be used to estimate the peak position (p) of the signal (with sub-pixel resolution) as described in Equation (4) below:

$$p = \text{angle}(H_1) \cdot W/(2\pi) \tag{4}$$

Changes in the calculated peak position (p) of the signal as indicated by the lateral movement of the reflected reference light received on linear image sensor 28 can then be used to determine the extent/amount of focus drift that has occurred and that therefore must be compensated for. That determined focus drift may then be compensated for by causing translation stage 26 to move in the axial direction in an amount that is based on the changed peak position. In the exemplary embodiment, a calibration curve is determined and employed to relate the peak position (p) linear image sensor 28 and the actual position of translation stage 26. So, overall, the estimated peak position (p) is just the position of translation stage 26. If there is no focus drift, the position of the signal should be stable in the period of imaging. If the position of the signal changes, that means that focus drift has occurred, which needs to be compensated for immediately using translation stage 26. In the non-limiting exemplary embodiment, the drift correction frequency is ~2 Hz, which means that the system tracks the position and compensates the drift two times per second. It will be appreciated, however, that this frequency can adjusted for different scenarios.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of disclosed concept which is to be given the full breadth of the claims appended and any and all equivalents thereof.

What is claimed is:

1. A method of compensating for focus drift in a microscopy system, the microscopy system including a lens system and a translation stage, the translation stage being structured to selectively move the lens system or a sample in an axial direction, the method comprising:

receiving data representing a reference light signal reflected from a sample and received by an image sensor;

identifying from the data a peak of the reference light signal, the peak having a maximum intensity value for the reference light signal;

extracting a sub-region having a center from the data, the center being located at the peak;

calculating a first harmonic of a Fourier transform of the extracted sub-region;

estimating a peak position of the reference light signal based on a phase of the first harmonic; and moving the lens system or the sample in the axial direction using the translation stage based on the estimated position.

2. The method according to claim 1, wherein the identifying the peak of the reference light signal comprises identifying a pixel of the image sensor having the maximum intensity value, wherein the center is located at the identified pixel having the maximum intensity value, and wherein the peak position is a sub-pixel peak position of the reference light signal.

3. The method according to claim 2, further comprising calculating a baseline (b) for reference light signal according to the following equation:

$$b = \min_{j=1:N}(I_j) + 0.1 \times \left(\max_{j=1:N}(I_j) - \min_{j=1:N}(I_j)\right),$$

where $I_j$ is an intensity of an jth pixel along the image sensor, wherein the image sensor has N pixels.

4. The method according to claim 3, wherein the sub-region has a half width of 3-5 times a Gaussian kernel width ($\sigma$) of the reference light signal.

5. The method according to claim 4, wherein $\sigma$ is estimated by the following equation:

$$\begin{cases} c = \sum_{I_j > b}(I_j - b)j / \sum_{I_j > b}(I_j - b) \\ \sigma = \sum_{I_j > b}(I_j - b)|j - c| / \sum_{I_j > b}(I_j - b) \end{cases},$$

where c is a centroid center of the reference light signal.

6. The method according to claim 1, wherein the sub-region has a width W, and wherein the first harmonic ($H_1$) is calculated using the following equation:

$$H_1 = \sum_{j=1}^{W} I_j \big( \cos(2\pi j/W) - i \cdot \sin(2\pi j/W) \big).$$

7. The method according to claim 6, wherein the peak position (p) is calculated using the following equation: p=angle ($H_1$)·W/($2\pi$).

8. A microscopy system, comprising:

a lens system;

a translation stage structured to selectively move the lens system or a sample in an axial direction;

an image sensor; and a control system structured and configured for compensating for focus drift in the microscopy system by:

receiving data representing a reference light signal reflected from a sample and received by the image sensor;

identifying from the data a peak of the reference light signal, the peak having a maximum intensity value for the reference light signal;

extracting a sub-region having a center from the data, the center being located at the peak;

calculating a first harmonic of a Fourier transform of the extracted sub-region;

estimating a peak position of the reference light signal based on a phase of the first harmonic; and moving the lens system or the sample in the axial direction using the translation stage based on the estimated position.

9. The microscopy system according to claim 8, wherein the identifying the peak of the reference light signal comprises identifying a pixel of the image sensor having the maximum intensity value, wherein the center is located at the identified pixel having the maximum intensity value, and wherein the peak position is a sub-pixel peak position of the reference light signal.

10. The microscopy system according to claim 9, wherein the control system is further structured and configured to calculate a baseline (b) for reference light signal according to the following equation:

$$b = \min_{j=1:N}(I_j) + 0.1 \times \Big( \max_{j=1:N}(I_j) - \min_{j=1:N}(I_j) \Big),$$

where $I_j$ is an intensity of an jth pixel along the image sensor, wherein the image sensor has N pixels.

11. The microscopy system according to claim 10, wherein the sub-region has a half width of 3-5 times a Gaussian kernel width ($\sigma$) of the reference light signal.

12. The microscopy system according to claim 11, wherein $\sigma$ is estimated by the following equation:

$$\begin{cases} c = \sum_{I_j > b}(I_j - b)j / \sum_{I_j > b}(I_j - b) \\ \sigma = \sum_{I_j > b}(I_j - b)|j - c| / \sum_{I_j > b}(I_j - b) \end{cases},$$

where c is a centroid center of the reference light signal.

13. The microscopy system according to claim 8, wherein the sub-region has a width W, and wherein the first harmonic ($H_1$) is calculated using the following equation:

$$H_1 = \sum_{j=1}^{W} I_j \big( \cos(2\pi j/W) - i \cdot \sin(2\pi j/W) \big).$$

14. The microscopy system according to claim 13, wherein the peak position (p) is calculated using the following equation: p=angle ($H_1$)·W/($2\pi$).

15. A microscopy system, comprising:

an automated sample labeling module structured and configured to label fluorescence dyes to biological structures of a sample;

a drift stabilization module structured and configured to actively track and compensate for focus drift of the microscopy system;

an illumination module structured and configured to generate a uniform illumination field for the microscopy system;

a detection module structured and configured to collect and record a fluorescence signal from the sample;

an automated sample positioning module structured and configured to control a 3D position of the sample; and a control system including:

(i) an automated sample labelling component comprising a number of first routines for controlling the automated sample labeling module;

(ii) a drift stabilization component comprising a number of second routines for controlling the drift stabilization module;

(iii) an illumination control component comprising a number of third routines for controlling the illumination module;

(iv) a detection component comprising a number of fourth routines for controlling the detection module; and (v) a sample positioning component comprising a number of fifth routines for controlling the automated sample positioning module.

16. The microscopy system according to claim 15, wherein the illumination module includes a lens system, wherein the drift stabilization module includes a translation stage and an image sensor, wherein the translation stage is operatively coupled to the lens system to selectively move the lens system in an axial direction, and wherein the second routines of the drift stabilization component compensate for the focus drift by:

receiving data representing a reference light signal reflected from a sample and received by the image sensor;

identifying from the data a peak of the reference light signal, the peak having a maximum intensity value for the reference light signal;

extracting a sub-region having a center from the data, the center being located at the peak;

calculating a first harmonic of a Fourier transform of the extracted sub-region;

estimating a peak position of the reference light signal based on a phase of the first harmonic; and moving the lens system in the axial direction using the translation stage based on the estimated position.

17. The microscopy system according to claim 16, wherein the identifying the peak of the reference light signal comprises identifying a pixel of the image sensor having the maximum intensity value, wherein the center is located at the identified pixel having the maximum intensity value, and wherein the peak position is a sub-pixel peak position of the reference light signal.

18. The microscopy system according to claim 16, wherein the sub-region has a half width of 3-5 times a Gaussian kernel width ($\sigma$) of the reference light signal.

19. The microscopy system according to claim 18, wherein $\sigma$ is estimated by the following equation:

$$
\begin{cases}
c = \sum_{I_j > b} (I_j - b) j / \sum_{I_j > b} (I_j - b) \\
\sigma = \sum_{I_j > b} (I_j - b) |j - c| / \sum_{I_j > b} (I_j - b)
\end{cases},
$$

where c is a centroid center of the reference light signal, and wherein b is a baseline for reference light signal determined according to the following equation:

$$
b = \min_{j=1:N}(I_j) + 0.1 \times \left( \max_{j=1:N}(I_j) - \min_{j=1:N}(I_j) \right),
$$

where $I_j$ is an intensity of an jth pixel along the image sensor, wherein the image sensor has N pixels.

20. The microscopy system according to claim 16, wherein the sub-region has a width W, and wherein the first harmonic ($H_1$) is calculated using the following equation:

$$
H_1 = \sum_{j=1}^{W} I_j \left( \cos(2\pi j/W) - i \cdot \sin(2\pi j/W) \right).
$$

21. The microscopy system according to claim 20, wherein the peak position (p) is calculated using the following equation: $p = \text{angle}(H_1) \cdot W/(2\pi)$.

22. A non-transitory computer readable medium storing one or more programs, including instructions, which when executed by a computer, causes the computer to perform the method of claim 1.

23. The method according to claim 1, wherein the image sensor is a linear image sensor.

24. The microscopy system according to claim 8, wherein the image sensor is a linear image sensor.

25. The microscopy system according to claim 16, wherein the image sensor is a linear image sensor.

\* \* \* \* \*